United States Patent
Ahmadian et al.

(10) Patent No.: US 8,940,857 B2
(45) Date of Patent: *Jan. 27, 2015

(54) METHODS AND COMPOSITIONS FOR ENHANCING DELIVERY OF DOUBLE-STRANDED RNA OR A DOUBLE-STRANDED HYBRID NUCLEIC ACID TO REGULATE GENE EXPRESSION IN MAMMALIAN CELLS

(75) Inventors: Mohammad Ahmadian, Bothell, WA (US); Kunyuan Cui, Bothell, WA (US); Lishan Chen, Bellevue, WA (US); Shu-Chih Chen, Seattle, WA (US); Michael E. Houston, Jr., Sammamish, WA (US)

(73) Assignee: Marina Biotech, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/870,989

(22) Filed: Aug. 30, 2010

(65) Prior Publication Data

US 2010/0316707 A1  Dec. 16, 2010

Related U.S. Application Data

(63) Continuation of application No. 12/013,274, filed on Jan. 11, 2008, which is a continuation of application No. 11/107,371, filed on Apr. 15, 2005, now abandoned.

(60) Provisional application No. 60/564,543, filed on Apr. 20, 2004.

(51) Int. Cl.
 A61K 38/00 (2006.01)
 C07H 21/04 (2006.01)
 C07H 21/02 (2006.01)
 A61K 9/127 (2006.01)

(52) U.S. Cl.
 USPC .......... 530/300; 536/23.1; 536/24.5; 424/450

(58) Field of Classification Search
 None
 See application file for complete search history.

(56) References Cited

U.S. PATENT DOCUMENTS 6,841,535 B2 * 1/2005 Divita et al. ............... 424/130.1
2004/0204377 A1 * 10/2004 Rana ............................. 514/44
2007/0020632 A1 * 1/2007 Tonelli et al. ................... 435/6

FOREIGN PATENT DOCUMENTS

WO  2004096826 A2  11/2004

OTHER PUBLICATIONS

Ethymiadis et al (J. Biol. Chem 273(3): 1623-1628, 1998).*
Efthymiadis et al., J. Biol. Chem. 273(3):1623-1628 (1998).

* cited by examiner

*Primary Examiner* — Richard Schnizer
(74) *Attorney, Agent, or Firm* — Lowe Graham Jones PLLC

(57) ABSTRACT

A delivery-enhancing peptide comprising the amino acid sequence of SEQ ID NO:11 or salt thereof. This invention is directed towards methods and compositions to administer a double-stranded ribonucleic acid to a mammal so as to effectuate transfection of the double-stranded RNA into a desired tissue of the mammal.

9 Claims, 4 Drawing Sheets

METHODS AND COMPOSITIONS FOR ENHANCING DELIVERY OF DOUBLE-STRANDED RNA OR A DOUBLE-STRANDED HYBRID NUCLEIC ACID TO REGULATE GENE EXPRESSION IN MAMMALIAN CELLS

CROSS REFERENCE TO RELATED APPLICATIONS

This application is a continuation of prior U.S. application Ser. No. 12/013,274, filed Jan. 11, 2008, which is a continuation of U.S. application Ser. No. 11/107,371, filed Apr. 15, 2005, which claims the benefit of U.S. Provisional Application No. 60/564,543, filed Apr. 20, 2004, each of which is incorporated herein by reference in its entirety.

SEQUENCE LISTING

This application includes a Sequence Listing submitted herewith via EFS-Web as an ASCII file created on Aug. 27, 2010, named MDR-04-02CON2_SeqList.txt, which is 8,316 bytes in size, and is hereby incorporated by reference in its entirety.

BACKGROUND OF THE INVENTION

RNA interference is the process of sequence-specific post transcriptional gene silencing in cells initiated by double-stranded RNA (dsRNA) that is homologous in sequence to a portion of a targeted mRNA. Introduction of dsRNA into cells leads to the destruction of the endogenous RNAs that share the same sequence as the dsRNA. The dsRNA molecules are cleaved by an RNase III family nuclease called Dicer into short-interfering RNAs (siRNA), which are 19-23 nucleotides (nt) in length. The siRNAs are incorporated into a multicomponent nuclease complex (RISC, RNA-induced silencing complex), which identifies mRNA substrates through their homology to the siRNA, binds to and destroys the targeted mRNA. In mammalian cells, dsRNAs longer than 30 base pairs can activate the dsRNA-dependent kinase PKR and 2'-5'-oligoadenylate synthetase, normally induced by interferon. By virtue of its small size, synthetic siRNA avoids activation of the interferon response. The activated PKR inhibits general translation by phosphorylation of the translation factor eukaryotic initiation factor $2\alpha$ (eIF2$\alpha$), while 2'-5'-oligoadenylate synthetase causes nonspecific mRNA degradation via activation of RNase L.

In contrast to the nonspecific effect of long dsRNA, siRNA can mediate selective gene silencing in the mammalian system Hairpin RNA with a short loop and 19 to 27 base pairs in the stem also selectively silences expression of genes that are homologous to the sequence in the double-stranded stem. Mammalian cells can convert short hairpin RNA into siRNA to mediate selective gene silencing.

RISC mediates cleavage of single stranded RNA having sequence complementary to the antisense strand of the siRNA duplex. Cleavage of the target RNA takes place in the middle of the region complementary to the antisense strand of the siRNA duplex.

Studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxy nucleotides (2'-H) was shown to be tolerated.

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity.

RNA interference is emerging as a promising means for reducing the expression of specific gene products, and thus may be useful for developing therapeutic drugs to treat viral infections, cancers, autoimmune diseases, and other diseases and conditions amenable to treatment by down-regulation of mRNA expression. However, there remains an important need in the art for additional tools and methods to design, produce, formulate, deliver, and use siRNAs as therapeutic tools, including for therapies targeted to specific tissues and cells.

DESCRIPTION OF EXEMPLARY EMBODIMENTS OF THE INVENTION

Figure 1:
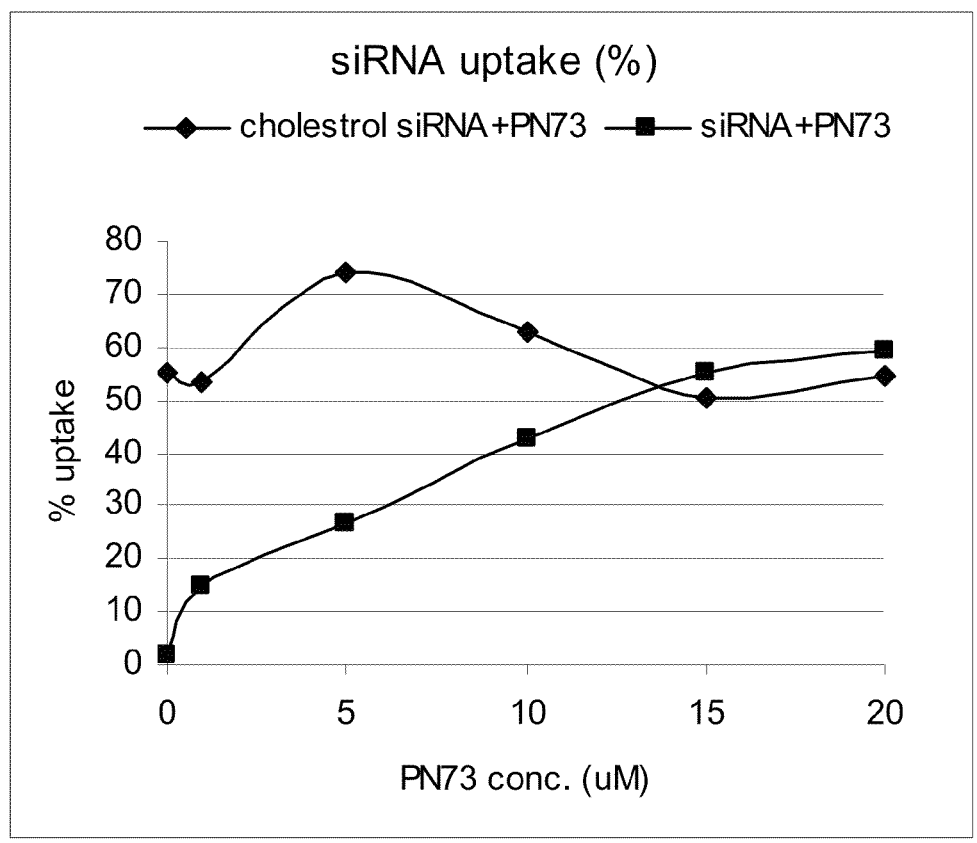
FIG. 1 illustrates serum effects on cellular uptake of a cholesterol-conjugated siRNA in complex with a delivery enhancing agent (comprising a permeabilizing peptide, PN73), and on an unconjugated siRNA in complex with PN73—expressed as percentage uptake.

The present invention fulfills these needs and satisfies additional objects and advantages by providing double-stranded nucleic acids conjugated to a cholesterol moiety to facilitate delivery of the nucleic acids into a selected target cell or tissue. In particular the present invention is directed towards methods and compositions to administer double-stranded ribonucleic acid to a mammal so as to effectuate transfection of the double-stranded RNA into a desired tissue of the mammal. In certain embodiments the double-stranded RNA has 30 or fewer nucleotides, and is a short interfering RNA (siRNA).

It has been surprisingly discovered that selectively conjugating a cholesterol moiety to a siRNA at selective ends of the siRNA sense and/or antisense strands increases the silencing of the targeted mRNA. For example, the following siRNA/cholesterol moiety constructs increase the silencing effect of the targeted mRNA in comparison to siRNA having no cholesterol conjugated to it:

1. A siRNA construct having a cholesterol moiety linked to the 5' end of the sense strand and the 5'end of the antisense, and no cholesterol moiety at the other ends;
2. A siRNA construct having a cholesterol moiety linked to the 3' end of the antisense strand, and no cholesterol moiety linked to the other ends of the siRNA strands;

3. A siRNA construct having cholesterol moiety linked to the 5' end of the sense strand, and no cholesterol moiety linked to the other ends of the siRNA strands;
4. A siRNA construct having a cholesterol moiety linked to the 3' end of the sense strand and no cholesterol moiety linked to the other ends of the siRNA strands;
5. A siRNA construct having a cholesterol moiety linked to the 3' end of the sense strand, a cholesterol moiety linked to the 3' end of the antisense strand and no cholesterol moiety linked to the other ends of the siRNA strands; and
6. A siRNA construct having a cholesterol moiety linked to the 5' end of the antisense strand and no cholesterol moiety linked to the other ends of the siRNA strands.

Thus, the constructs listed above are embodiments of the present invention, as well as those constructs in which the ds nucleic acid is a siHybrid in which the sense strand is a DNA molecule.

The following constructs showed a progressively decreased silencing of the targeted mRNA in comparison to a siRNA having no cholesterol moieties conjugated to any of its ends:
1. A siRNA construct having a cholesterol moiety linked to the 3' end of the sense strand, a cholesterol moiety linked 5'end of the antisense strand and no cholesterol moiety linked to the other ends of the siRNA strands;
2. A siRNA construct having a cholesterol moiety linked to the 3'end of the antisense strand, a cholesterol moiety linked to the 5' end of the antisense strand and no cholesterol moiety linked to the other ends of the siRNA strands;
3. A siRNA construct having a cholesterol moiety linked to the 5' end of the sense strand a cholesterol moiety linked to the 3' end of the antisense strand and no cholesterol moiety linked to the other ends of the siRNA strands;
4. A siRNA construct having a cholesterol moiety linked to 5' end of the sense strand, a cholesterol moiety linked to the 3' end of the sense strand, and no cholesterol moiety linked to the other ends of the siRNA strands;
5. A siRNA construct having a cholesterol moiety linked to 5' end of the sense strand, a cholesterol moiety linked to the 3' end of the antisense strand, a cholesterol moiety linked to the 5' end of the antisense strand and no cholesterol moiety linked to the 3' end of the sense strand;
6. A siRNA construct having a cholesterol moiety linked to 5' end of the sense strand, a cholesterol moiety linked to the 3' end of the sense strand, a cholesterol moiety linked to the 3' end of the antisense strand and no cholesterol moiety linked to the 5' end of the antisense strand;
7. A siRNA construct having a cholesterol moiety linked to 5' end of the sense strand, a cholesterol moiety linked to the 3' end of the sense strand, a cholesterol moiety linked to the 5' end of the antisense strand and no cholesterol moiety linked to the 3' end of the antisense strand;
8. A siRNA construct having a cholesterol moiety linked to 3' end of the sense strand, a cholesterol moiety linked to the 3' end of the sense strand, a cholesterol moiety linked to the 3' end of the antisense strand, a cholesterol moiety linked to the 5' end of the antisense strand, and no cholesterol moiety linked to the 5' end of the sense strand;
9. A siRNA construct having a cholesterol moiety on the 5' end of the sense strand, a cholesterol moiety on the 3' end of the sense strand, a cholesterol moiety on the 3' end of the antisense strand and a cholesterol moiety on the 5' end of the antisense strand.

Definitions

As used herein, the term "inverted repeat" refers to a nucleic acid sequence comprising a sense and an antisense element positioned so that they are able to form a double stranded siRNA when the repeat is transcribed. The inverted repeat may optionally include a linker or a heterologous sequence such as a self-cleaving ribozyme between the two elements of the repeat. The elements of the inverted repeat have a length sufficient to form a double stranded RNA. Typically, each element of the inverted repeat is about 15 to about 100 nucleotides in length, preferably about 20-30 base nucleotides, preferably about 20-25 nucleotides in length, e.g., 20, 21, 22, 23, 24, 25, 26, 27, 28, 29, or 30 nucleotides in length.

"Silencing" refers to partial or complete loss-of-function through targeted inhibition of gene expression in a cell and may also be referred to as "knock down". Depending on the circumstances and the biological problem to be addressed, it may be preferable to partially reduce gene expression. Alternatively, it might be desirable to reduce gene expression as much as possible. The extent of silencing may be determined by any method known in the art, some of which are summarized in International Publication No. WO 99/32619. Depending on the assay, quantitation of gene expression permits detection of various amounts of inhibition for example, greater than 10%, 33%, 50%, 90%, 95% or 99%.

The phrase "inhibiting expression of a target gene" refers to the ability of a siRNA of the invention to initiate gene silencing of the target gene. To examine the extent of gene silencing, samples or assays of the organism of interest or cells in culture expressing a particular construct are compared to control samples lacking expression of the construct. Control samples (lacking construct expression) are assigned a relative value of 100% Inhibition of expression of a target gene is achieved when the test value relative to the control is about 90%, preferably 50%, more preferably 25-0%. Suitable assays include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

"Large double-stranded RNA" refers to any double-stranded RNA having a size greater than about 40 base pairs (bp) for example, larger than 100 by or more particularly larger than 300 bp. The sequence of a large dsRNA may represent a segment of a mRNA or the entire mRNA. The maximum size of the large dsRNA is not limited herein. The double-stranded RNA may include modified bases where the modification may be to the phosphate sugar backbone or to the nucleoside. Such modifications may include a nitrogen or sulfur heteroatom or any other modification known in the art.

The double-stranded structure may be formed by self-complementary RNA strand such as occurs for a hairpin or a micro RNA or by annealing of two distinct complementary RNA strands.

"Overlapping" refers to when two RNA fragments have sequences which overlap by a plurality of nucleotides on one strand, for example, where the plurality of nucleotides (nt) numbers as few as 2-5 nucleotides or by 5-10 nucleotides or more.

"One or more dsRNAs" refers to dsRNAs that differ from each other on the basis of sequence.

"Target gene or mRNA" refers to any gene or mRNA of interest. Any of the genes previously identified by genetics or by sequencing can be implemented as a target. Target genes or mRNA can include developmental genes and regulatory genes, as well as metabolic or structural genes or genes encoding enzymes. The target gene may be expressed in cells in which a phenotype is being investigated, or in an organism in a manner that directly or indirectly impacts a phenotypic characteristic. The target gene may be endogenous or exogenous. Such cells include any cell in the body of an adult or embryonic animal or plant including gamete or any isolated cell such as occurs in an immortal cell line or primary cell culture.

In this specification and the appended claims, the singular forms of "a", "an" and "the" include plural reference unless the context clearly dictates otherwise.

"siRNA" means a small interfering RNA that is a short-length double-stranded RNA that are not toxic in mammalian cells. The length is not limited to 21 to 23 bp long. There is no particular limitation in the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription product of siRNA to be expressed can be, for example, 15 to 49 bp, preferably 15 to 35 bp, and more preferably 21 to 30 bp long. The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. Nonpairing portions can be contained to the extent that they do not interfere with siRNA formation. The "bulge" used herein preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA enables to silence the target gene expression due to its RNAi effect. The cohesive (overhanging) end structure is not limited only to the 3' overhang as reported by Tuschl et al. (ibid.), and the 5' overhanging structure may be included as long as it is capable of inducing the RNAi effect. In addition, the number of overhanging nucleotides is not limited to the reported 2 or 3, but can be any numbers as long as the overhang is capable of inducing the RNAi effect. For example, the overhang may be 1 to 8, or 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as the siRNA is able to maintain its gene silencing effect on the target gene, it may comprise a low molecular weight RNA (which may be a natural RNA molecule such as tRNA, rRNA or viral RNA, or an artificial RNA molecule), for example, in the overhanging portion at its one end.

In addition, the terminal structure of the "siRNA" is necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA or viral RNA, or an artificial RNA molecule.

"Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form siRNA. These antisense and sense RNAs have been conventionally synthesized with an RNA synthesizer.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo. Optionally, the siRNA include single strands or double strands of siRNA.

An siHybrid molecule is a double-stranded nucleic acid that has a similar function to siRNA. Instead of a double-stranded RNA molecule, a siHybrid is comprised of an RNA strand and a DNA strand. Preferably, the RNA strand is the antisense strand as that is the strand that binds to the target mRNA. The siHybrid created by the hybridization of the DNA and RNA strands have a hybridized complementary portion and preferably at least one 3'overhanging end.

A cholesterol moiety is a cholesterol molecule, sterol or any compound derived from cholesterol including cholestanol, ergosterol, stimastanol, stigmasterol, methyl-litho-cholic acid, cortisol, corticosterone, $\Delta^5$-pregnenolone, progesterone, deoxycorticosterone, 17-OH-pregnenolone, 17-OH-progesterone, 11-dioxycortisol, dehydroepiandrosterone, dehydroepiandrosterone sulfate, androstenedione, aldosterone, 18-hydroxycorticosterone, tetrahydrocortisol, tetrahydrocortisone, cortisone, prednisone, 6α-methylprednisone, 9α-fluoro-16α-hydroxyprednisolone, 9α-fluoro-16α-methylprednisolone, 9α-fluorocortisol, testosterone, dihydrotestosterone, androstenediol, androstenedione, androstenedione, 3α,5α-androstanediol, estrone, estradiol, estrogen, spermidine cholesterol carbamate, $N^4$-spermidine cholesteryl carbamate, $N^4$-spermidine cholesteryl carbamate di HCl salt, $N^4$-spermidine-7 dehydro cholesteryl carbamate, N4-spermine cholesteryl carbamate, N,N bis(3-aminopropyl)cholesteryl carbamate, N,N bis(6-aminohexyl)cholesteryl carbamate, $N^4$-spermidine dihydrocholesteryl carbamate, $N^4$-spermidine lithocholic carbamate methyl ester, $N^1,N^8$-bis(3-aminopropyl-$N^4$-spermidine cholesteryl carbamate, $N(N^4$-3 aminopropylspermidine)cholesteryl carbamate, N,N-bis(4-aminobutyl)cholesteryl carbamate, $N^4$-spermidine cholesteryl urea, $N^4$-spermine cholesteryl urea, $N^4$-spermidine dihydro cholesteryl urea, $N^4$-spermine dihydro cholesteryl urea, N,N-bis(N'-3-aminopropyl-N"4-aminobutyl)cholesteryl carbamate, N4spermidine cholesteryl carboxamide, and N-[$N^1$, $N^4$, $N^8$-tris(3-aminopropyl) spermidine]cholesteryl carbamate, lumisterol, cholic acid, desoxycholic acid, chenodesoxycholic acid and lithocholic acid and derivatives thereof (see, e.g., U.S. Pat. No. 6,331,524).

The following exemplary cholesterol-RNA constructs are illustrative of various embodiments of the invention:

1. A siRNA or siHybrid construct having a cholesterol moiety linked to the 5' end of the sense strand and the 5'end of the antisense and no cholesterol moiety at the other ends;
2. A siRNA or siHybrid construct having a cholesterol moiety linked to the 3' end of the antisense strand and no cholesterol moiety linked to the other ends of the siRNA or siHybrid strands;
3. A siRNA or siHybrid construct having cholesterol moiety linked to the 5' end of the sense strand and no cholesterol moiety linked to the other ends of the siRNA or siHybrid strands;
4. A siRNA or siHybrid construct having a cholesterol moiety linked to the 3' end of the sense strand and no cholesterol moiety linked to the other ends of the siRNA or siHybrid strands;
5. A siRNA or siHybrid construct having a cholesterol moiety linked to the 3' end of the sense strand, a cholesterol moiety linked to the 3' end of the antisense strand and no cholesterol moiety linked to the other ends of the siRNA or siHybrid strands; and
6. A siRNA or siHybrid construct having a cholesterol moiety linked to the 5' end of the antisense strand and no cholesterol moiety linked to the other ends of the siRNA or siHybrid strands.

In more detailed embodiments of the invention, a cholesterol-conjugated siRNA or siHybrid is formulated with, or delivered in a coordinate administration method with, one or more secondary delivery-enhancing agent(s) that is/are further effective to enhance delivery of the cholesterol-conjugated siRNA or siHybrid into mammalian cells. Typically the second delivery-enhancing agent(s) is/are effective to facilitate delivery of the cholesterol-conjugated siRNA or siHybrid across the plasma membrane and into the cytoplasm of a targeted mammalian cell. The targeted cell may be any cell for which delivery of a cholesterol-conjugated siRNA or siHybrid into the cell for regulation of gene expression is desired. Exemplary target cells in this context include pulmonary alveolar or other airway cells, skin cells, hepatic cells, renal cells, pancreatic cells, endothelial cells, nucleated blood cells (e.g., lymphocytes, monocytes, macrophages, or dendritic cells), muscle cells (e.g., cardiac or smooth muscle cells), mammary cells, peripheral or central nervous system (CNS) cells, cells of the stomach or intestinal tract, tumor cells, and other cells that are amenable to gene regulation for therapeutic purposes according to the methods and compositions of the invention.

In on exemplary embodiment, the cholesterol-conjugated siRNA or siHybrid are targeted for delivery to mucosal epithelial cells, for example nasal mucosal epithelial cells.

Within these and related aspects of the invention, the secondary delivery-enhancing agent(s) may be selected from one or any combination of the following:

(a) an aggregation inhibitory agent;
(b) a charge modifying agent;
(c) a pH control agent;
(d) a degradative enzyme inhibitory agent;
(e) a mucolytic or mucus clearing agent;
(f) a ciliostatic agent;
(g) a membrane penetration-enhancing agent selected from (i) a surfactant, (ii) a bile salt, (iii) a phospholipid additive, mixed micelle, liposome, or carrier, (iv) an alcohol, (v) an enamine, (vi) an NO donor compound, (vii) a long-chain amphipathic molecule (viii) a small hydrophobic penetration enhancer; (ix) sodium or a salicylic acid derivative; (x) a glycerol ester of acetoacetic acid (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, or (xviii) an inhibitor of cholesterol synthesis; or (xix) any combination of the membrane penetration enhancing agents recited in (g)(i)-(xix);
(h) a delivery-enhancing peptide;
(i) a vasodilator agent;
(j) a selective transport-enhancing agent; and
(k) a stabilizing delivery vehicle, carrier, support or complex-forming species with which the cholesterol-conjugated siRNA or siHybrid is effectively combined, associated, contained, encapsulated or bound resulting in stabilization of the siRNA or siHybrid for enhanced delivery.

In additional aspects of the invention, the delivery-enhancing agent(s) comprise(s) any one or any combination of two or more of the foregoing delivery-enhancing agents recited in (a)-(k), and the formulation of the cholesterol-conjugated siRNA or siHybrid with the delivery-enhancing agents provides for increased delivery of the cholesterol-conjugated siRNA or siHybrid into the cytoplasm of target cells for gene regulation by the cholesterol-conjugated siRNA or siHybrid.

Any one or combination of the foregoing secondary delivery-enhancing agents may be added to a pharmaceutical composition comprising a cholesterol-conjugated siRNA or siHybrid as described herein, to yield a combinatorial formulation providing greater delivery enhancement in comparison to intracellular delivery of the cholesterol-conjugated siRNA or siHybrid without the secondary delivery-enhancing agent(s).

Within coordinate administration methods of the invention, the cholesterol-conjugated siRNA or siHybrid is administered to a target cell, tissue, or individual in combination with one or more secondary delivery-enhancing agents in a coordinate administration protocol. Within these coordinate administration methods, the cholesterol-conjugated siRNA or siHybrid is administered to the same cell, tissue, or individual as the secondary delivery-enhancing agent(s), prior to, simultaneous with, or after administration of the secondary delivery-enhancing agent(s), which similarly may be selected from any one or combination of the following:

(a) an aggregation inhibitory agent;
(b) a charge modifying agent;
(c) a pH control agent;
(d) a degradative enzyme inhibitory agent;
(e) a mucolytic or mucus clearing agent;
(f) a ciliostatic agent;
(g) a membrane penetration-enhancing agent selected from (i) a surfactant, (ii) a bile salt, (iii) a phospholipid additive, mixed micelle, liposome, or carrier, (iv) an alcohol, (v) an enamine, (vi) an NO donor compound, (vii) a long-chain amphipathic molecule (viii) a small hydrophobic penetration enhancer; (ix) sodium or a salicylic acid derivative; (x) a glycerol ester of acetoacetic acid (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, or (xviii) an inhibitor of cholesterol synthesis; or (xix) any combination of the membrane penetration enhancing agents recited in (g)(i)-(xix);
(h) a delivery-enhancing peptide;
(i) a vasodilator agent;
(j) a selective transport-enhancing agent; and
(k) a stabilizing delivery vehicle, carrier, support or complex-forming species with which the cholesterol-conjugated siRNA or siHybrid is effectively combined, associated, contained, encapsulated or bound resulting in stabilization of the siRNA or siHybrid for enhanced intracellular delivery. The coordinate administration of the cholesterol-conjugated siRNA or siHybrid and secondary delivery-enhancing agent(s) provides for increased uptake of the cholesterol-conjugated siRNA or siHybrid into the cytoplasm of targeted cells, typically enhancing gene regulation (e.g., increasing knockdown of mRNA translation to thereby reduce expression of one or more selected protein(s), such as TNF-α, in the target cell.

Additional detailed description pertaining to secondary delivery-enhancing agents, for use within the instant invention is provided, for example, in U.S. Provisional Patent Applications Nos. 60/612,121, filed Sep. 21, 2004; 60/667, 835, filed Apr. 1, 2005; 60/612,285, filed Sep. 21, 2004; 60/667,871, filed Apr. 1, 2005; 60/613,416, filed Sep. 27, 2004; and 60/667,833, filed Apr. 1, 2005, each incorporated herein by reference.

Within exemplary embodiments of the invention, a delivery-enhancing peptide is employed as the secondary delivery-enhancing agent. The delivery-enhancing peptide may be conjugated to, combinatorially formulated with, or coordinately administered with, the cholesterol-conjugated siRNA or siHybrid to enhance intracellular uptake of the cholesterol-conjugated siRNA or siHybrid and improve gene regulation results achieved thereby. Delivery-enhancing peptides in this context may include natural or synthetic, therapeutically or prophylactically active, peptides (comprised of two or more covalently linked amino acids), proteins, peptide or protein fragments, peptide or protein analogs, peptide or protein mimetics, and chemically modified derivatives or salts of active peptides or proteins. Thus, as used herein, the term "delivery-enhancing peptide" will often be intended to embrace all of these active species, i.e., peptides and proteins, peptide and protein fragments, peptide and protein analogs, peptide and protein mimetics, and chemically modified derivatives and salts of active peptides or proteins. Often, the delivery-enhancing peptide comprises a mutein that is readily obtainable by partial substitution, addition, or deletion of amino acids within a naturally occurring or native (e.g., wild-type, naturally occurring mutant, or allelic variant) peptide or protein sequence (e.g., a sequence of a naturally occurring "cell penetrating peptide" or peptide fragment of a native protein, such as a tight junction protein). Additionally, biologically active fragments of native peptides or proteins are included. Such mutant derivatives and fragments substantially retain the desired cell penetrating or other delivery-enhancing activity of the corresponding native peptide or proteins. In the case of peptides or proteins having carbohydrate chains, biologically active variants marked by alterations in these carbohydrate species are also included within the invention.

The delivery-enhancing peptides, proteins, analogs and mimetics for use within the methods and compositions of the invention are may be conjugated to, or formulated with, the cholesterol-conjugated siRNA or siHybrid to yield a pharmaceutical composition that includes a delivery-enhancing effective amount of the delivery-enhancing peptide, protein, analog or mimetic (i.e., an amount of the peptide sufficient to detectably enhance intracellular delivery of the cholesterol-conjugated siRNA or siHybrid).

Exemplary delivery-enhancing peptides for use within the methods and compositions of the invention include any one or combination of the following peptides, or active fragments, muteins, conjugates, or complexes thereof:

```
                                              (SEQ ID NO: 1)
    RKKRRQRRRPPQCAAVALLPAVLLALLAP;

(SEQ ID NO: 2)
    RQIKIWFQNRRMKWKK;

(SEQ ID NO: 3)
    GWTLNSAGYLLGKINLKALAALAKKIL;

(SEQ ID NO: 4)
    KLALKLALKALKAALKLA;

(SEQ ID NO: 7)
    KLWSAWPSLWSSLWKP;

(SEQ ID NO: 8)
    AAVALLPAVLLALLAPRKKRRQRRRPPQ;

(SEQ ID NO: 9)
    LLETLLKPFQCRICMRNFSTRQARRNHRRRHRR;

(SEQ ID NO: 10)
    RRRQRRKRGGDIMGEWGNEIFGAIAGFLG;

(SEQ ID NO: 11)
    KETWWETWWTEWSQPGRKKRRQRRRPPQ;

(SEQ ID NO: 12)
    GLGSLLKKAGKKLKQPKSKRKV;
    and (SEQ ID NO: 13)
    KGSKKAVTKAQKKDGKKRKRSRKESYSVYVYKVLKQ
```

Delivery-enhancing peptides of the invention may further include various modifications known in the art, e.g., for modifying the charge, membrane permeability, half-life, degradative potential, reactivity (e.g., to form conjugates), immunogenicity, or other desired properties of the subject peptide. Exemplary modified delivery-enhancing peptides in this context may include, for example, peptides modified by incorporation of one or more selected amino- or carboxy-terminal chemical modifications. For example, amino- and/or carboxy-terminal amide, BrAc, or maleimide groups may be included, as exemplified by the modified delivery-enhancing peptides shown in Table 1.

TABLE 1

| Peptide | Sequences | Effects |
|---|---|---|
| PN0028 | RKKRRQRRRPPQCAAVALLPAVLLALLAP-amide (SEQ ID NO: 1) | + |
| PN0058 | RQIKIWFQNRRMKWKK-amide (SEQ ID NO: 2) | + |
| PN0064 | BrAc-GWTLNSAGYLLGKINLKALAALAKKILamide (SEQ ID NO: 3) | + |
| PN0068 | BrAc-KLALKLALKALKAALKLA-amide (SEQ ID NO: 4) | + |
| PN0069 | GRKKRRQRRRPQ-amide (SEQ ID NO: 5) | − |
| PN0071 | RRRRRRR (SEQ ID NO: 6) | − |
| PN0228 | NH2-KLWSAWPSLWSSLWKP-amide (SEQ ID NO: 7) | +/− |
| PN027 | NH2-AAVALLPAVLLALLAPRKKRRQRRRPPQ-amide (SEQ ID NO: 8) | + |
| PN202 | NH2-LLETLLKPFQCRICMRNFSTRQARRNHRRRHRR-amide (SEQ ID NO: 9) | + |
| PN250 | NH2-RRRQRRKRGGDIMGEWGNEIFGAIAGFLG-amide (SEQ ID NO: 10) | + |
| PN183 | NH2-KETWWETWWTEWSQPGRKKRRQRRRPPQ-amide (SEQ ID NO: 11) | + |
| PN283 | Maleimide-GLGSLLKKAGKKLKQPKSKRKV-amide (SEQ ID NO: 12) | + |
| PN073 | KGSKKAVTKAQKKDGKKRKRSRKESYSVYVYKVLKQ-amide (SEQ ID NO: 13) | + |

Assay Medium Only

The + and − notations indicated in Table 1 for the listed peptides relate to activity of the peptides to enhance permeation of across epithelial monolayers—as determined by measurement of peptide-mediated changes in trans-epithelial electrical resistance (TEER). A + notation indicates that the subject peptide enhances epithelial permeation of macromolecules. The peptides that exhibit permeation-enhancing activity can be tested and selected according to the methods herein to determine their utility for enhancing delivery of cholesterol-conjugated siRNA or siHybrid into the cytoplasm of targeted cells to enhance gene regulation The above disclosure generally describes the present invention, which is further exemplified by the following examples. These examples are described solely for purposes of illustration, and are not intended to limit the scope of the invention. Although specific terms and values have been employed herein, such terms and values will likewise be understood as exemplary and non-limiting to the scope of the invention.

Example 1

Synthesis and Purification of Cholesterol-Labeled siRNA

Synthesis of Unmodified siRNAs:

Unmodified siRNAs were synthesized according to the general strategy for solid-phase oligonucleotide synthesis. The syntheses proceeded from the 3'- to 5'-direction [current protocols in nucleic acid chemistry, chapter 3]. The first step involved attachment of a mononucleoside/tide to the surface of an insoluble solid support through a covalent bond. All unmodified siRNAs described here were synthesized starting with a CPG-bound deoxythymidine (purchased from Glen Research, Sterling Va.). The thymidine nucleoside is covalently attached to the solid support through 3'-hydroxyl group using a base labile linker. Before chain elongation can proceed, the terminal-protecting group (dimethoxytrityl, DMT) on the nucleoside is removed. This exposes a free 5'-OH group where the next nucleotide unit can be added. An excess of reagents is used to force the coupling reaction to occur on as many of the immobilized nucleotides as possible. After the coupling reaction, excess reagents are washed away. The reaction is followed by a c capping step, to block off non-extended sites, and an oxidation step. The process of terminal-protecting group removal and chain extension is then repeated using different bases until the desired sequence has been assembled. Some or all of the protecting groups may optionally be removed, and then the covalent attachment to the support is hydrolyzed to release the product. Removal of the protecting groups were carried out with 3:1 mixture of concentrated ammonia:ethanol. After removal of any remaining protecting groups, the oligonucleotide is ready for purification and use.

RNA syntheses were carried out by Applied Biosystems 3400 using standard phosphoramidite chemistry. The corresponding building blocks, 5'-dimethoxytrityl-N-benzoyladenosine-2'-O-(t-butyldimethylsilyl)-3'-[(2-cyanoethyl)-(N,N-diisopropyl)]-phosphoramidite (Bz-A-CE phosphoramidite) (I), 5'-dimethoxytrityl-N-dimethylformamidine-guanosine, 2'-O-(t-butyldimethylsilyl)-3'-[(2-cyanoethyl)-(N,N-diisopropyl)]-phosphoramidite (dmf-G-CE phosphoramidite) (II), 5'-dimethoxytrytiyl-N-acetylcytidine-2'-O-(t-butyldimethylsilyl)-3'-[(2-cyanoethyl)-(N,N-diisopropyl)]-phosphoramidite (Ac—C—CE phosphoramidite) (III), 5-dimethoxytrityluridine-2'-O-(t-butyldimethylsilyl)-3'-[(2-cyanoethyl)-(N,N-diisopropyl)]-phosphoramidite (U—CE phosphoramidite) (IV) and 5'-dimethoxytrityl-2'-deoxythymidine-3'-[(2-cyanoethyl)-(N,N-diisopropyl)]-phosphoramidite (V) were purchased from Glen Research Inc. (Sterling Va.). For un-modified sequences, the syntheses started on Controlled Pore glass (CPG) bound deoxytimidine (VI) (Applied Biosystems, Foster City, Calif.) in 0.2 or 1.0 μmol scale. Other reagents and solvents were purchased from Glen Research (Sterling, Va.) and/or Applied Biosystems (Foster City, Calif.).

I

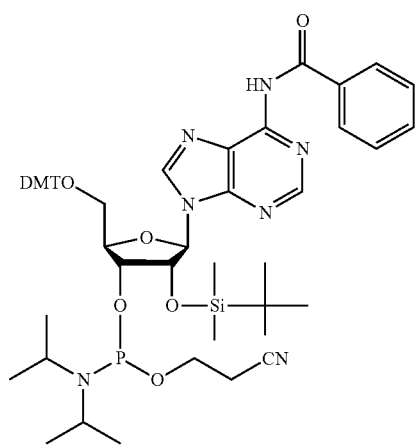

II

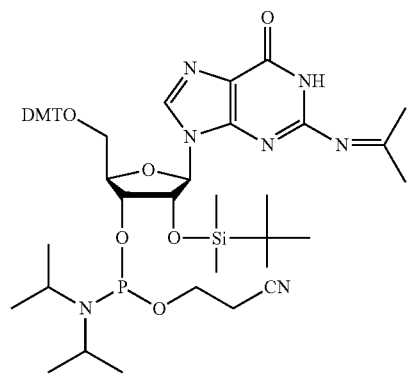

III

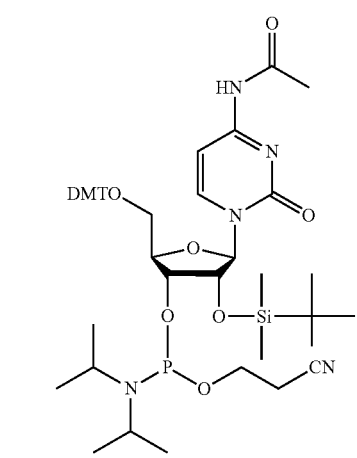

IV

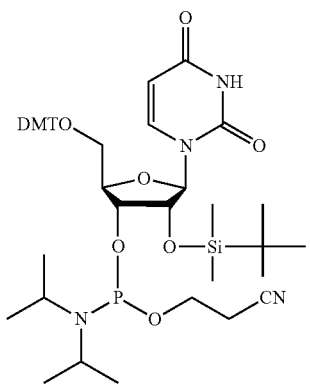

V

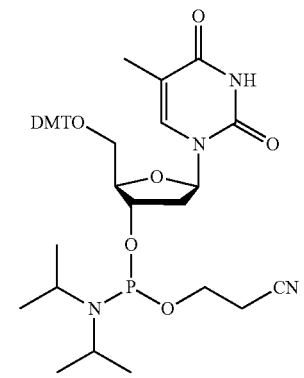

VI

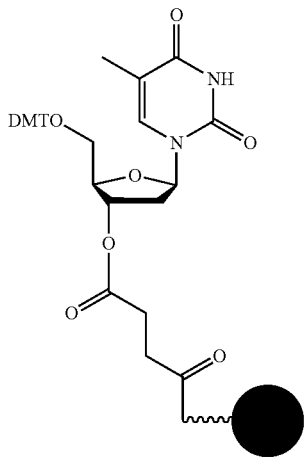

DMT=4,4'-dimethoxytrytyl
Commonly used protected phosphoramidites for the synthesis of RNA
Synthesis of 3'-cholesteryl-Labeled siRNA The synthesis of 3'-cholestery-labelled siRNAs was carried out using the modified support strategy. In this method a new modified solid phase synthesis support must be prepared for ach 3'-reporter group or conjugate. The solid phase support for attaching cholesteryl group to the 3'-termini of oligonucleotides is commercially available. The synthesis of the 3'-cholesteryl-labelled oligonucleotides were accomplished using 1-dimethoyxytrityloxy-3-O—(N-cholesteryl-3-aminopropyl)-triethyleneglycol-glyceryl-2-O-succinoyl-long-chain-alkylamino-CPG (VII, Glen Research, Sterling Va.). The designed 21 nucleotide sequence was then assembled on this modified solid support using standard phosphoramidite protocols for RNA synthesis as described herein above.

Synthesis of 5'-cholesteryl-Labeled siRNA

A protected oligonucleotide with a free hydroxyl group at the 5'-end, immobilized on the solid support, may easily be obtained by solid phase synthesis using either methodologies described herein above. The 5'-terminal hydroxyl can then be reacted with phosphoramidites. Phosphoramidites often obtained from a molecule having a hydroxyl functionality allow the direct introduction of a functional group or ligand to the chain after oxidation and deprotection. To incorporated a cholesteryl group to the 5'-end of siRNA molecules, dimethoxytrityloxy-3-O—(N-cholesteryl-3-aminopropyl)-triethyleneglycol-glyceryl-2-O-(2-cyanoethyl)-(N,N,-diisopropyl)-phosphoramidite (VIII) was purchased from Glen Research (Sterling, Va.). During the solid support synthesis of siRNA, after the incorporation of the last nucleoside/tide, the 5'-dimethoyxtrytyl protecting group was cleaved and VIII was coupled to the grown chain

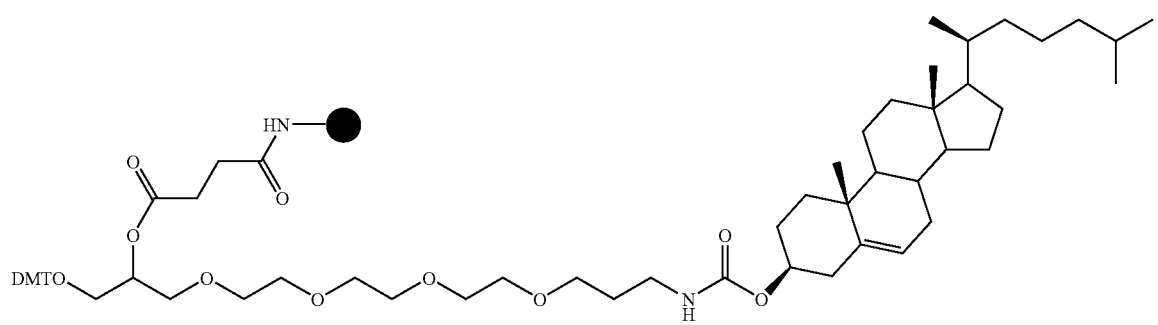

1-dimethoyxytrityloxy-3-O—(N-cholesteryl-3-aminopropyl)-triethyleneglycol-glyceryl-2-O-succinoyl-long-chain-alkylamino-CPG (VII)

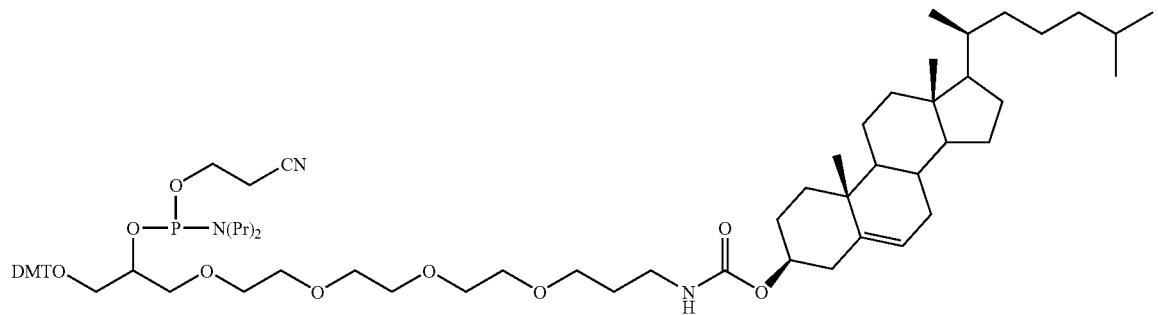

dimethoxytrityloxy-3-O—(N-cholesteryl-3-aminopropyl)-triethyleneglycol-glyceryl-2-O-(2-cyanoethyl)-(N,N,-diisopropyl)-phosphoramidite (VIII)

Syntheses of 3' and 5'-dicholesteryl-Labeled siRNAs

Syntheses of 3',5'-dicholesteryl-labeled siRNAs were accomplished using a combination of the methods described above. The synthesis of such a molecule started with using VII as the "modified solid support", and elongation and incorporation of the 5'-cholesteryl moiety were carried out as described above.

Example 2

Cholesterol-Enhanced Uptake of siRNA and Silencing of Beta-Galactosidase mRNA Expression Transfection of 9L/LacZ Cells:
Day 0:
a) Take saturated 9L/LacZ culture from T75 flask, detach cell and dilute into 10 ml with complete medium (DMEM, 1× PS, 1× Na Pyruvate, 1× NEAA).
b) Further dilute the cell to 1:15, and seed 100 μl into each 96 well, which should give 50% confluence cell the next day for transfection. Remember to leave the edge well empty and fill with 250 μl water, do not stack up plates in the incubator.
c) Incubate overnight at 37° C., 5% $CO_2$ incubator.

Day 1:
a) Prepare the transfection complex in Opti-MEM, 50 μl each well.
b) Dump the medium in plates, wash each well once with 200 μl PBS or Opti-MEM.
c) Blot the plates dry completely with tissue by inversion.
d) Add the transfection mixture (50 μl/well) into each well, add 250 μl water into wells on the edge to prevent wells from drying.
e) Incubate for at least 3 hours at 37° C., 5% $CO_2$ incubator.
f) Dump the transfection mixture, replace with 100 μl of complete medium (DMEM, 1× PS, 1× Na Pyruvate, 1× NEAA).

β-Gal/BCA Assay in 96 Well Format
Cell Lysis
a) Dump the medium, wash once with 200 μl PBS, blot the plate dry with inversion.
b) Add 30 μl lysis buffer from β-Gal Kit into each well.
c) Freeze-Thaw the cells twice to generate lysate.

β-Gal Assay
a) Prepare assay mix (50 μl 1× buffer, 17 μl ONPG each well)
b) Take new plate and add 65 ul assay mix into each well.
c) Add 10 μl of cell lysate into each well. There should be blank wells for subtraction of the background activities.
d) Incubate at 37° C. for about 20 minutes, prevent long incubation which will use up all ONPG and biased the high expression.
e) Add 100 μl of the Stop solution.
f) Measure the OD at 420 nm.

BCA Assay
a) Prepare BSA standard (150 ul per well), every points should be duplicated on each plate.
b) Put 145 μl of water into each well, add 5 ul of cell lysate into each well.
c) Prepare Assay Reagent (A:B:C: 25:24:1), mix right before use.
d) Add 150 μl of Assay Reagent into each well.
e) Incubate at 37° C. for about 20 minutes.
f) Measure the OD at 562 nm.

Flow Cytometry Measurement of FITC/FAM Conjugated siRNA
a) After transfection, incubate cell for at least 3 hours.
b) Wash with 200 μl PBS.
c) Detach cell with 15 μl TE, incubate at 37° C.
d) Re-suspend five wells with 30 μl FACS solution (PBS with 0.5% BSA, and 0.1% sodium Azide)
e) Combine all five wells into a tube.
f) Add PI 5 μl into each tube.
g) Analyze the cells with fluorescence activated cell sorting (FCAS) with BD FACscan instrument according to manufacture's instruction.

Results

Cholesterol Conjugation of siRNA

The transfection was performed with either regular siRNA or cholesterol-conjugated siRNA with lipofectamine (Invitrogen) on 9L/beta-gal cells. The siRNA was designed to specifically knock down beta-galactosidase mRNA and activities are expressed as percentage of beta-gal activities from control (transfected cells by lipofectamine alone).

```
1.    siRNA sequence and structure information
      of cholesterol-conjugated siRNA
                                          (SEQ ID NO: 14)
      C.U.A.C.A.C.A.A.A.U.C.A.G.C.G.A.U.U.U.dT.dT
      (Sense)

(SEQ ID NO: 15)
      A.A.A.U.C.G.C.U.G.A.U.U.U.G.U.G.U.A.G.dT.dT
      (Antisense)
```

Designation of cholesterol conjugated siRNA
A. regular sense or antisense strand
B. 5' end labeled sense strand
C. 3' end labeled sense strand
D. both ends labeled sense strand
E. 5' end labeled antisense strand
F. 3' end labeled antisense strand
G. both end labeled antisense strand Sense (B)

(SEQ ID NO: 16)

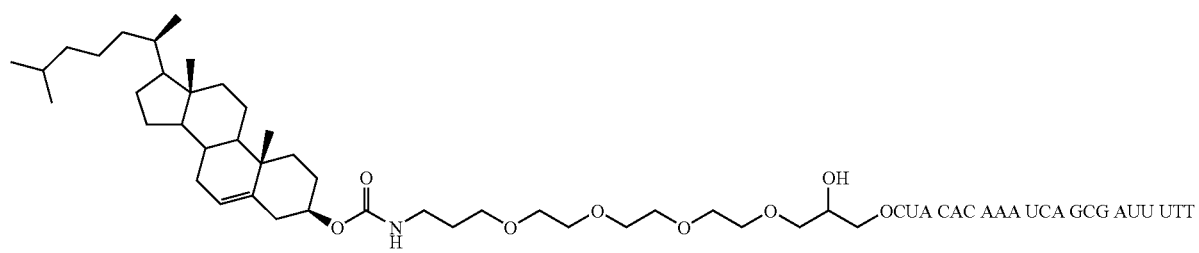

Sense (C)

(SEQ ID NO: 17)

CUA CAC AAA UCA GCG AUU UTT -[cholesterol-PEG linker conjugate]

Sense (D)

(SEQ ID NO: 18)

[cholesterol-PEG linker conjugate]- OPO₃ CUACACAAAUCAGCGAUUUTT—

Antisense (E)

(SEQ ID NO: 19)

[cholesterol-PEG linker conjugate]-OAAA UCG CUG AUU UGU GUA GTT

Antisense (F)

(SEQ ID NO: 20)

AAA UCG CUG AUU UGU GUA GTT-O-[linker with OH, PEG, carbamate]-O-Cholesterol

Antisense (G)

(SEQ ID NO: 21)

Cholesterol-O-C(=O)-NH-(CH2)3-(O-CH2CH2)4-O-CH2-CH(OH)-CH2-OPO3-AAAUCGCUGAUUUGUGUAGTT—

[Structure with phosphate, OH, PEG linker, carbamate, and cholesterol]

TABLE 1

Cholesterol siRNA Activities Post-Transfection

| Duplexes | Activity (% of control) |
|---|---|
| AA | 23.12 |
| BE | 10.27 |
| AF | 11.99 |
| BA | 12.09 |
| CA | 16.18 |
| CF | 16.76 |
| AE | 19.02 |
| CE | 27.62 |
| AG | 29.87 |
| BF | 32.02 |
| DA | 33.99 |
| BG | 46.39 |
| DF | 65.4 |
| DE | 77.12 |
| CG | 77.80 |
| DG | 98.84 |

Table 1 above provides results of transfection and mRNA silencing experiments using the siRNA constructs made using sense and antisense strands designated above. The transfection and silencing assay results show cholesterol-enhanced delivery of exemplary siRNAs of the invention, and demonstrate silencing of the beta-galactosidase mRNA by the cholesterol-conjugated siRNAs. The "Activity (% of control)" indicates the beta-galactosidase activity remaining after the transfection. The lower the percentage, the greater was the efficacy of the siRNA construct. The double letters represent a double-stranded siRNA. Thus, the exemplary constructs, BE, AF, BA, CA, CF, and AE are representative of the nature and activity of cholesterol conjugated dsRNAs of the present invention. These constructs show greater silencing efficacy than the corresponding unconjugated siRNAs. siRNA constructs CE, AG, BF, DA, BG, DF, DE, CG and DG showed lower efficacy than the unconjugated siRNA construct AA.

AA is a siRNA construct with no cholesterol conjugated to any of the ends of the sense or antisense RNA strands. This construct was transfected into the cells resulting in silencing of the beta-galactosidase mRNA so that 23.12% of the activity of the beta-galactosidase mRNA remained.

BE is a siRNA construct having a cholesterol moiety linked to the 5' end of the sense strand and a cholesterol moiety linked to the 5'end of the antisense strand, and no cholesterol moiety linked to the other ends of the siRNA. This construct was transfected into the cells resulting in silencing the beta-galactosidase mRNA so that only 10.27% of the activity of the beta-galactosidase mRNA remained. This is unexpectedly superior to the unconjugated siRNA.

AF is a siRNA construct having a cholesterol moiety linked to the 3' end of the antisense strand and no cholesterol moiety linked to the other ends of the siRNA strands. This construct was transfected into the cells resulting in silencing the beta-galactosidase mRNA so that only 11.99% of the activity of the beta-galactosidase mRNA remained. This is unexpectedly superior to the unconjugated siRNA.

BA is a siRNA construct having a cholesterol moiety linked to the 5' end of the sense strand and no cholesterol moiety linked to the other ends of the siRNA strands. This construct was transfected into the cells resulting in silencing the beta-galactosidase mRNA so that only 12.09% of the activity of the beta-galactosidase mRNA remained. This is unexpectedly superior to the unconjugated siRNA.

CA is a siRNA construct having a cholesterol moiety linked to the 3' end of the sense strand and no cholesterol moiety linked to the other ends of the siRNA strands. This construct was transfected into the cells resulting in silencing the beta-galactosidase mRNA so that only 16.18% of the activity of the beta-galactosidase mRNA remained. This is unexpectedly superior to the unconjugated siRNA.

CF is a siRNA construct having a cholesterol moiety linked to the 3' end of the sense strand, a cholesterol moiety linked to the 3' end of the antisense strand, and no cholesterol moiety linked to the other ends of the siRNA strands. This construct was transfected into the cells resulting in silencing the beta-galactosidase mRNA so that only 16.76% of the activity of the beta-galactosidase mRNA remained. This is unexpectedly superior to the unconjugated siRNA.

AE is a siRNA construct having a cholesterol moiety linked to the 5' end of the antisense strand and no cholesterol moiety linked to the other ends of the siRNA strands. This construct was transfected into the cells resulting in silencing the beta-galactosidase mRNA so that only 19.02% of the activity of the beta-galactosidase mRNA remained. This is unexpectedly superior to the unconjugated siRNA.

The constructs listed below showed lower ability to silence the beta-galactosidase reporter than was determined for the corresponding, unconjugated siRNA.

CE is a siRNA construct having a cholesterol moiety linked to the 3' end of the sense strand, a cholesterol moiety linked 5'end of the antisense strand, and no cholesterol moiety linked to the other ends of the siRNA strands. This construct was transfected into the cells resulting in silencing the beta-galactosidase mRNA so that 27.62% of the activity of the beta-galactosidase mRNA remained. This silencing effect was lower than that observed for the corresponding, unconjugated siRNA.

AG is a siRNA construct having a cholesterol moiety linked to the 3'end of the antisense strand, a cholesterol moiety linked to the 5' end of the antisense strand, and no cholesterol moiety linked to the other ends of the siRNA strands. This construct was transfected into the cells resulting in silencing the beta-galactosidase mRNA so that 29.87% of the activity of the beta-galactosidase mRNA remained. This silencing effect was lower than that observed for the corresponding, unconjugated siRNA.

BF is a siRNA construct having a cholesterol moiety linked to the 5' end of the sense strand, a cholesterol moiety linked to the 3' end of the antisense strand, and no cholesterol moiety linked to the other ends of the siRNA strands. This construct was transfected into the cells resulting in silencing the beta-galactosidase mRNA so that 32.02% of the activity of the beta-galactosidase mRNA remained. This silencing effect was lower than that observed for the corresponding, unconjugated siRNA.

DA is a siRNA construct having a cholesterol moiety linked to 5' end of the sense strand, a cholesterol moiety linked to the 3' end of the sense strand, and no cholesterol moiety linked to the other ends of the siRNA strands. This construct was transfected into the cells resulting in silencing the beta-galactosidase mRNA so that 33.99% of the activity of the beta-galactosidase mRNA remained. This silencing effect was lower than that observed for the corresponding, unconjugated siRNA.

BG is a siRNA construct having a cholesterol moiety linked to 5' end of the sense strand, a cholesterol moiety linked to the 3' end of the antisense strand, a cholesterol moiety linked to the 5' end of the antisense strand, and no cholesterol moiety linked to the 3' end of the sense strand. This construct was transfected into the cells resulting in silencing the beta-galactosidase mRNA so that 46.39% of the activity of the beta-galactosidase mRNA remained. This silencing effect was lower than that observed for the corresponding, unconjugated siRNA.

DF is a siRNA construct having a cholesterol moiety linked to 5' end of the sense strand, a cholesterol moiety linked to the 3' end of the sense strand, a cholesterol moiety linked to the 3' end of the antisense strand, and no cholesterol moiety linked to the 5' end of the antisense strand. This construct was transfected into the cells resulting in silencing the beta-galactosidase mRNA so that 65.40% of the activity of the beta-galactosidase mRNA remained. This silencing effect was lower than that observed for the corresponding, unconjugated siRNA.

DE is a siRNA construct having a cholesterol moiety linked to 5' end of the sense strand, a cholesterol moiety linked to the 3' end of the sense strand, a cholesterol moiety linked to the 5' end of the antisense strand and no cholesterol moiety linked to the 3' end of the antisense strand. This construct was transfected into the cells resulting in silencing the beta-galactosidase mRNA so that 77.12% of the activity of the beta-galactosidase mRNA remained. This silencing effect was lower than that observed for the corresponding, unconjugated siRNA.

BG is a siRNA construct having a cholesterol moiety linked to 3' end of the sense strand, a cholesterol moiety linked to the 3' end of the sense strand, a cholesterol moiety linked to the 3' end of the antisense strand, a cholesterol moiety linked to the 5' end of the antisense strand, and no cholesterol moiety linked to the 5' end of the sense strand. This construct was transfected into the cells resulting in silencing the beta-galactosidase mRNA so that 77.80% of the activity of the beta-galactosidase mRNA remained. This silencing effect was lower than that observed for the corresponding, unconjugated siRNA.

DG is a siRNA construct having a cholesterol moiety on the 5' end of the sense strand, a cholesterol moiety on the 3' end of the sense strand, a cholesterol moiety on the 3' end of the antisense strand, and a cholesterol moiety on the 5' end of the antisense strand. This construct was transfected into the cells resulting in silencing the beta-galactosidase mRNA so that 98.84% of the activity of the beta-galactosidase mRNA remained. This silencing effect was lower than that observed for the corresponding, unconjugated siRNA.

Example 3

Serum Inhibition of Cholesterol-Enhanced siRNA Uptake, and Rescue of Cholesterol Enhancement of Uptake by Additional Delivery-Enhancing Agents Human Monocyte Isolation and Purity Fresh human blood samples from healthy donors were purchased from Golden West Biologicals (Temecula, Calif.). For isolation of monocytes, blood samples were diluted with PBS at 1:1 ratio immediately after receiving. Peripheral blood mononuclear cells (PBMC) were first isolated by Ficoll (Amersham, Calif., USA) gradient from whole blood. Then monocytes were further purified from PBMCs using Miltenyi CD14 positive selection kit (MILTENYI BIOTEC GmbH, Germany) by following the manufacturer's instructions. The purity of the monocytes was greater than 95%, judged by flow cytometry stained with anti-CD14 antibody (BD Biosciences, Calif.). Purified human monocytes were maintained overnight in complete media before induction and knockdown assay.

Flow Cytometry

Fluorescence activated cell sorting (FACS) analysis were performed using Beckman Coulter FC500 cell analyzer (Fullerton, Calif.). The instrument was adjusted according to the fluorescence probes used (FAM or Cy5 for siRNA and FITC and PE for CD14). Propidium iodide (Fluka, St Lois, Mo.) and AnnexinV (R&D systems, Minneapolis, Minn.) were used as indicators for cell viability and cytotoxicity.

For siRNA uptake analysis, cells were washed with PBS, treated with trypsin (attached cells only), and then analyzed by flow cytometry. Uptake of the siRNA designated BA, described above, was also measured by intensity of Cy5 or FAM fluorescence in the cells and cellular viability assessed by addition of propidium iodide or AnnexinV-PE. In order to differentiate the cellular uptake from the membrane insertion of fluorescence labeled siRNA, trypan blue was used to quench the fluorescence on the cell membrane surface.

TABLE 2

Higher MFI with PN73 compared with cholesterol siRNA alone

| Serum | Cholesterol siRNA alone | Unconjugated siRNA with 20 µM PN73 |
| --- | --- | --- |
| 0 | 24.8 | 32.9 |
| 5% | 1.55 | 11.5 |
| 10% | 1.34 | 6.39 |
| 20% | 1.19 | 5.85 |

The data in Table 2 show that the presence of serum significantly reduces cellular uptake of the siRNA conjugated to a cholesterol moiety according to the invention. Serum also inhibits unconjugated siRNA uptake in the presence of an exemplary delivery-enhancing peptide, PN73

(KGSKKAVTKAQKKDGKKRKRSRKESYSVYVYKVLKQ-amide; SEQ ID NO: 13), but to a lesser extent than the inhibition noted for the cholesterol-conjugated siRNA.

Figure 2:
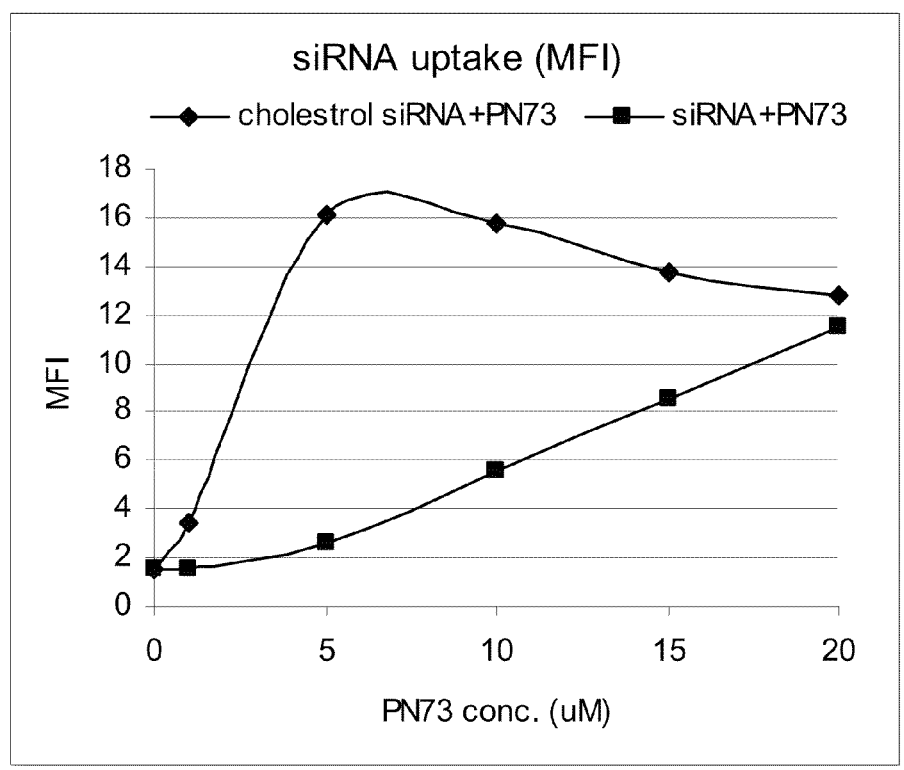
FIG. 2 illustrates serum effects on cellular uptake of a cholesterol-conjugated siRNA in complex with PN73, and on an unconjugated siRNA in complex with PN73-expressed as mean fluorescence intensity (MFI).

FIGS. 1 and 2 illustrate the effects of 5% serum on cellular uptake of a cholesterol-conjugated siRNA according to the invention in complex with a permeabilizing peptide delivery enhancing agent, PN73 (cholesterol siRNA+PN73), and on an unconjugated siRNA in complex with PN73 (siRNA+PN73). For these and related uptake assays, cholesterol-conjugated siRNA and siRNA/PN73 complex were transfected into human monocytes in Opti-MEM® media (Invitrogen) as described above, with serum added in fixed or varied concentration(s). The final concentration of siRNA for both cholesterol and complex were 0.2 µM. The uptake efficiency and Mean fluorescence intensity were assessed by flow cytometry. The cellular uptake values shown in FIGS. 1 and 2 were determined with variation of PN73 concentrations in the presence of a fixed, 5% concentration of serum.

Figure 3:
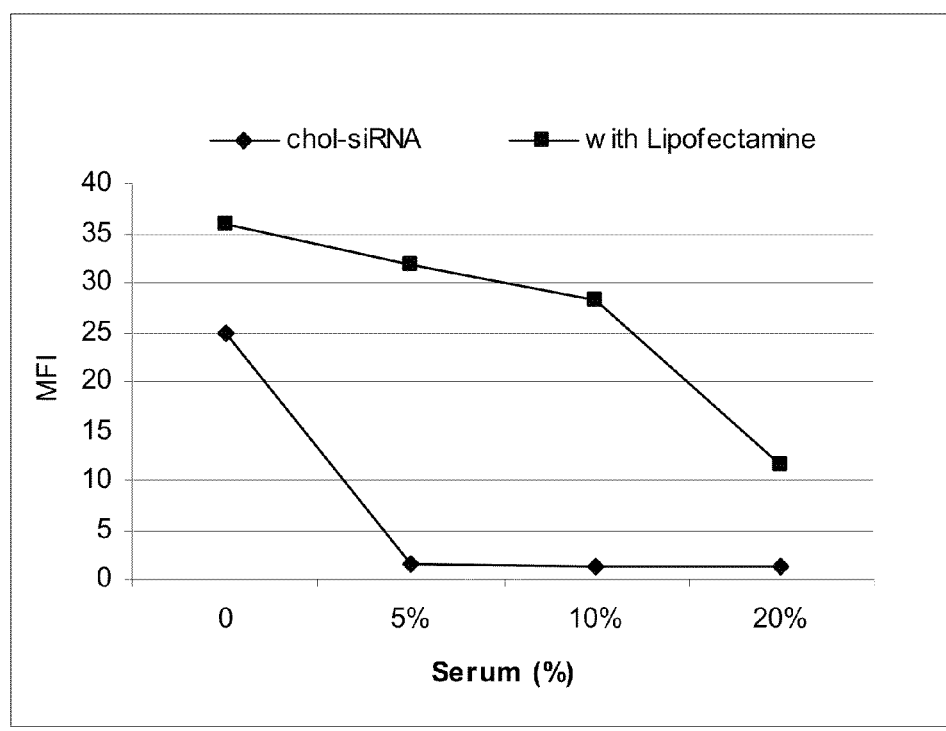
FIG. 3 illustrates the effects of increasing concentrations of serum on cellular uptake of a cholesterol-conjugated siRNA in the presence or absence of a second delivery enhancing agent, lipofectamine-expressed as percentage uptake.
Figure 4:
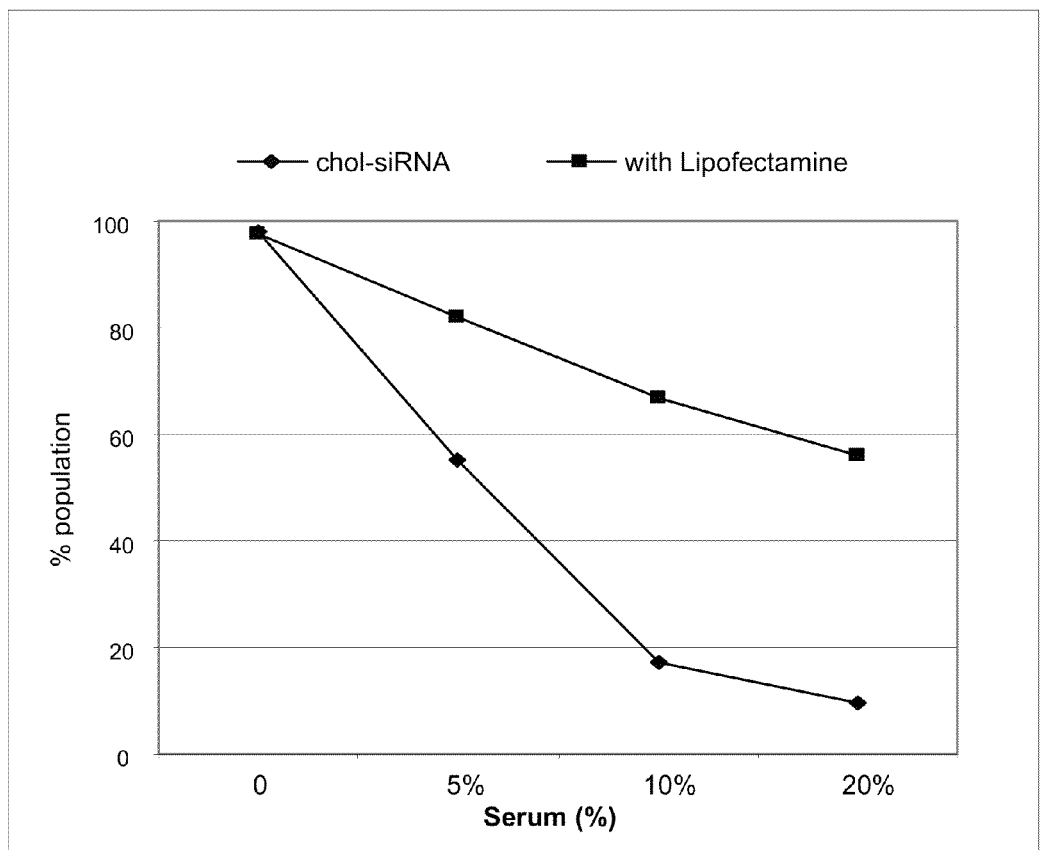
FIG. 4 illustrates the effects of increasing concentrations of serum on cellular uptake of a cholesterol-conjugated siRNA in the presence or absence of a second delivery enhancing agent, lipofectamine-expressed as MFI.

FIGS. 3 and 4 illustrate the effects of varying concentrations of serum on cellular uptake of a cholesterol-conjugated siRNA in the presence or absence of a second delivery enhancing agent, lipofectamine, as determined by flow cytometry.

The foregoing studies demonsrate that cholesterol-conjugation of siRNAs can significantly enhance their cellular uptake. However, uptake of cholesterol-conjugated siRNAs can be substantially diminished or even eliminated by the presence of serum. This is likely due to binding of the cholesterol moiety with serum proteins—inhibiting the ability of the cholesterol-bound siRNAs to enter target cells. In the presence of a selected delivery enhancing agent, Lipofectamine, this inhibitory effect of serum on cholesterol-siRNA uptake can be effectively diminished. In addition, the presence of a different kind of delivery enhancing agent, exemplified by the permeabilizing peptide PN73, can also mediate rescue of siRNA delivery blocked by serum. More specifically, the addition of a permeabilizing peptide to a delivery formulation comprising a siRNA conjugated to a cholesterol moiety reduces the inhibitory effects of serum on cholesterol-siRNA uptake in a dose dependent manner. This discovery indicates that, although cholesterol conjugation to siRNA alone may not optimize siRNA delivery, additional delivery-enhancing agents including, but not limited to, Lipofectamine and PN73, can further enhance siRNA delivery to mammalian cells and tissues in vitro and in vivo.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

What is claimed is:

1. A delivery-enhancing peptide comprising the amino acid sequence of SEQ ID NO: 11 or salt thereof.

2. The delivery-enhancing peptide of claim 1, wherein the delivery-enhancing peptide is modified by incorporation of one or more amino- and/or carboxy-terminal chemical modifications.

3. The delivery-enhancing peptide of claim 2, wherein the one or more amino- and/or carboxy-terminal chemical modifications are selected from the group consisting of an amide, BrAc, and maleimide group.

4. A composition comprising a delivery-enhancing peptide comprising the amino acid sequence of SEQ ID NO: 11 or salt thereof, and a nucleic acid.

5. The composition of claim 4, wherein the nucleic acid is a single stranded nucleic acid or a double-stranded nucleic acid.

6. The composition of claim 4, wherein the nucleic acid comprises RNA and/or DNA.

7. The composition of claim 4, wherein the nucleic acid is an siRNA or siHybrid.

8. The composition of claim 4, wherein the delivery-enhancing peptide is in a complex with the nucleic acid or is conjugated to the nucleic acid.

9. The composition of claim 4 further comprising a surfactant, liposome, long chain amphipathic molecule, cyclodextrin, chelating agent, amino acid or salt thereof, or any combination thereof.

* * * * *

SEQUENCE LISTING

<160> NUMBER OF SEQ ID NOS: 21

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      HIV virus and Homo sapiens construct

<400> SEQUENCE: 1

Arg Lys Lys Arg Arg Gln Arg Arg Pro Pro Gln Cys Ala Ala Val
 1               5                  10                  15

Ala Leu Leu Pro Ala Val Leu Leu Ala Leu Leu Ala Pro
            20                  25

<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Gln Asn Arg Arg Met Lys Trp Lys Lys
 1               5                  10                  15

<210> SEQ ID NO 3
<211> LENGTH: 27
<212> TYPE: PRT
<213> ORGANISM: Unknown Organism
<220> FEATURE:
<223> OTHER INFORMATION: Description of Unknown Organism: Human, swine,
      or mouse, and wasp venom

<400> SEQUENCE: 3

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Leu Ala Leu Lys Leu Ala Leu Lys Ala Leu Lys Ala Ala Leu Lys
 1               5                  10                  15

Leu Ala

<210> SEQ ID NO 5
<211> LENGTH: 12
<212> TYPE: PRT
<213> ORGANISM: Human immunodeficiency virus

<400> SEQUENCE: 5

Gly Arg Lys Lys Arg Arg Gln Arg Arg Arg Pro Gln
 1               5                  10

<210> SEQ ID NO 6
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Arg Arg Arg Arg Arg Arg Arg
1               5

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Leu Trp Ser Ala Trp Pro Ser Leu Trp Ser Ser Leu Trp Lys Pro
1               5                   10                  15

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      HIV virus and Homo sapiens construct

<400> SEQUENCE: 8

Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln
            20                  25

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Leu Glu Thr Leu Leu Lys Pro Phe Gln Cys Arg Ile Cys Met Arg
1               5                   10                  15

Asn Phe Ser Thr Arg Gln Ala Arg Arg Asn His Arg Arg Arg His Arg
            20                  25                  30

Arg

<210> SEQ ID NO 10
<211> LENGTH: 29
<212> TYPE: PRT
<213> ORGANISM: Influenza virus

<400> SEQUENCE: 10

Arg Arg Arg Gln Arg Arg Lys Arg Gly Gly Asp Ile Met Gly Glu Trp
1               5                   10                  15

Gly Asn Glu Ile Phe Gly Ala Ile Ala Gly Phe Leu Gly
            20                  25

<210> SEQ ID NO 11
<211> LENGTH: 28
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 11

Lys Glu Thr Trp Trp Glu Thr Trp Trp Thr Glu Trp Ser Gln Pro Gly
 1               5                  10                  15

Arg Lys Lys Arg Arg Gln Arg Arg Pro Pro Gln
            20                  25

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Gly Ser Leu Leu Lys Lys Ala Gly Lys Lys Leu Lys Gln Pro
 1               5                  10                  15

Lys Ser Lys Arg Lys Val
            20

<210> SEQ ID NO 13
<211> LENGTH: 36
<212> TYPE: PRT
<213> ORGANISM: Homo sapiens

<400> SEQUENCE: 13

Lys Gly Ser Lys Lys Ala Val Thr Lys Ala Gln Lys Lys Asp Gly Lys
 1               5                  10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
<223> OTHER INFORMATION: Description of Artificial Sequence: Synthetic
      siRNA oligonucleotide construct

<400> SEQUENCE: 14
cuacacaaau cagcgauuut t                                           21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
<223> OTHER INFORMATION: Description of Artificial Sequence: Synthetic
      siRNA oligonucleotide construct

<400> SEQUENCE: 15
aaaucgcuga uuuguguagt t                                           21

<210> SEQ ID NO 16
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
<223> OTHER INFORMATION: Description of Artificial Sequence: Synthetic
      siRNA oligonucleotide construct
<220> FEATURE:
<223> OTHER INFORMATION: 5' end labeled sense strand

<400> SEQUENCE: 16
cuacacaaau cagcgauuut t                                                    21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
<223> OTHER INFORMATION: Description of Artificial Sequence: Synthetic
      siRNA oligonucleotide construct
<220> FEATURE:
<223> OTHER INFORMATION: 3' end labeled sense strand

<400> SEQUENCE: 17
cuacacaaau cagcgauuut t                                                    21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
<223> OTHER INFORMATION: Description of Artificial Sequence: Synthetic
      siRNA oligonucleotide construct
<220> FEATURE:
<223> OTHER INFORMATION: both ends labeled sense strand

<400> SEQUENCE: 18
cuacacaaau cagcgauuut t                                                    21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
<223> OTHER INFORMATION: Description of Artificial Sequence: Synthetic
      siRNA oligonucleotide construct
<220> FEATURE:
<223> OTHER INFORMATION: 5' end labeled antisense strand

<400> SEQUENCE: 19
aaaucgcuga uuuguguagt t                                                    21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
```

```
<223> OTHER INFORMATION: Description of Artificial Sequence: Synthetic
      siRNA oligonucleotide construct
<220> FEATURE:
<223> OTHER INFORMATION: 3' end labeled antisense strand

<400> SEQUENCE: 20
aaaucgcuga uuuguguagt t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA oligonucleotide construct
<220> FEATURE:
<223> OTHER INFORMATION: Description of Artificial Sequence: Synthetic
      siRNA oligonucleotide construct
<220> FEATURE:
<223> OTHER INFORMATION: both ends labeled antisense strand

<400> SEQUENCE: 21
aaaucgcuga uuuguguagt t                                              21
```